United States Patent [19]

Sakamoto et al.

[11] 4,205,081
[45] May 27, 1980

[54] COMPOSITION AND METHOD FOR PREVENTING OR TREATING SWINE DYSENTERY

[75] Inventors: Koji Sakamoto; Takeshi Asano, both of Takasaki; Kazuo Mizuochi, Tokyo; Kanemichi Sasaki, Koshigaya, all of Japan

[73] Assignees: Nippon Kayaku Kabushiki Kaisha; Chugai Seiyaku Kabushiki Kaisha, both of Tokyo, Japan

[21] Appl. No.: 7,794

[22] Filed: Jan. 30, 1979

[30] Foreign Application Priority Data

Jan. 31, 1978 [JP] Japan .................................. 53-8827

[51] Int. Cl.$^2$ ............................................ A61K 31/335
[52] U.S. Cl. ................................................... 424/279
[58] Field of Search ......................................... 424/279

[56] References Cited

U.S. PATENT DOCUMENTS 3,777,023  12/1973  Sagawa et al. ...................... 424/200

OTHER PUBLICATIONS

Messersmith, Chem. Abst., vol. 87 (1977), p. 62, 863p.

*Primary Examiner*—Frederick E. Waddell

[57] ABSTRACT

A composition comprising one or more kinds of macrotetrolide antibiotic substances represented by the following general formula:

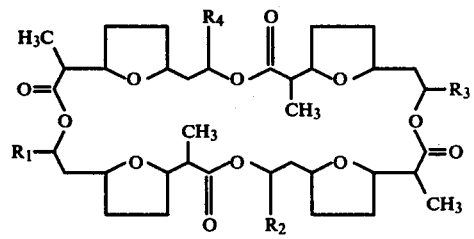

wherein $R_1$, $R_2$, $R_3$ and $R_4$ are lower alkyl groups, and a physiologically acceptable carrier is effective for preventing and treating swine dysentery.

7 Claims, No Drawings

COMPOSITION AND METHOD FOR PREVENTING OR TREATING SWINE DYSENTERY

This invention relates to a composition and a method for preventing and treating swine dysentery. More particularly, this invention relates to a composition for preventing and treating swine dysentery which comprises one or more kinds of macrotetrolide antibiotic substances represented by the following general formula (I):

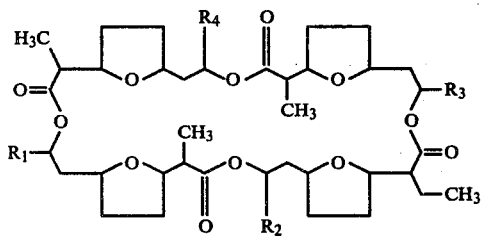

wherein $R_1$, $R_2$, $R_3$ and $R_4$ are lower alkyl groups, and a physiologically acceptable carrier, as well as to a method for preventing and treating swine dysentery by the use of said composition.

Swine dysentery is an infectious disease of swine caused by the oral infection with Treponema hyodysenteriae which attacks the large intestine to excrete mucous and bloody stools, lessens the feed efficiency and delays the growth to reduce productivity.

At the present time, swine is intensively raised as herd. If swine dysentery occurs once, accordingly, it propagates to all the animals to cause mucous and bloody stools and thereby lessens the feed efficiency and delays the growth to a great extent, which is a great economical loss in swine raising.

At the present stage, synthetic bactericides such as Carbadox, Panazon and the like or antibiotics such as Tylosin, Spiramycin and the like are used for the prevention and treatment of swine dysentery. However, they have problems in respect of safety such as carcinogenecity and persistency, so that they are limited in usability.

The present inventors have conducted extensive studies about the agent for preventing and treating swine dysentery and, as the result, have found that the compound represented by the general formula (I) is excellent as an agent for preventing and treating swine dysentery.

This invention has been accomplisehd on the basis of the above-mentioned finding.

Thus it is an object of this invention to provide a novel composition for preventing and treating swine dysentery.

It is another object of this invention to provide a novel method for preventing and treating swine dysentery.

Other objects and advantages of this invention will become apparent from the descriptions given below.

The macrotetrolide antibiotic substances used in this invention, represented by the general formula (I), are disclosed compounds which are mentioned in, for example, Helvetica Chimica Acta 38, 1445–1448 (1955), ibid. 45, 129–138 (1962) and ibid. 45, 620–630 (1962) and can be produced by cultivating Streptomyces aureus (FERM-P No. 233, ATCC 21428) in a nutrient medium (U.S. Pat. No. 3,743,724). They are known as insecticide or miticide (U.S. Pat. No. 3,777,023).

These antibiotic substances include some substances which are the same in formula but are a little different from one another in physical and chemical properties depending on the process of production or purification and therefore are considered stereoisomers one another. However, any of those substances can be used in this invention without discrimination.

Typical examples of the compounds represented by the general formula (I) are shown in Table 1.

Table 1

| Compound No. Name | 1 Nonactin | 2 Monactin | 3 Dinactin | 4 Trinactin | 5 Tetranactin |
|---|---|---|---|---|---|
| $R_1$ | $CH_3$ | $C_2H_5$ | $C_2H_5$ | $C_2H_5$ | $C_2H_5$ |
| $R_2$ | $CH_3$ | $CH_3$ | $C_2H_5$ | $C_2H_5$ | $C_2H_5$ |
| $R_3$ | $CH_3$ | $CH_3$ | $CH_3$ | $C_2H_5$ | $C_2H_5$ |
| $R_4$ | $CH_3$ | $CH_3$ | $CH_3$ | $CH_3$ | $C_2H_5$ |
| mp (°C.) | 148–149 | 63–64 | 73–74 | 79–80 | 105–106 |

These compounds have so low a toxicity that its acute oral toxicity $LD_{50}$ is 25000 mg/kg or more to mouse, 2500 mg/kg or more to rat and 2000 mg/kg or more to quail. This means that they have a very high safety.

The macrotetrolide antibiotic substance represented by the above-mentioned genral formula (I), obtainable by cultivating Streptomyces aureus, is usually in the state of a mixture of which main constituents are dinactin, trinactin and tetranactin. This mixture is called under the general name of "polynactin".

The composition of this invention for preventing and treating swine dysentery can be produced by admixing the compound represented by the aforementioned general formula (I) with a physiologically harmless solid or liquid carrier. This composition contains the active ingredient in an amount of 10 ppm or more and preferably in an amount of 1000 ppm or more.

Examples of the solid carrier used herein include crude wheat meal, crude soybean meal, corn starch, defatted rice bran, calcium carbonate, talc, kaolinite, chalk, diatomaceous earth and the like. Examples of the liquid carrier include water, isotonic sodium chloride solution and the like. Besides above, adjuvants and additives such as emulsifier, dispersing agent, suspension stabilizer, wetting agent and the like may also be used, if necessary.

In administering the composition of this invention to swine for the purpose of preventing and treating swine dysentery, it is sufficient to administer it continuously at a dose of 0.2 to 20 mg active ingredient per day per 1 kg of swine body weight. Actually, it is practical and economical to mix the composition with feed so that the proportion of active ingredient becomes 10–1000 ppm and then administer the mixture to swine continuously.

Otherwise, the composition of this invention for preventing and treating swine dysentery may also be administered directly in the form of solid preparation such as tablet, capsule, granule, pellet, bolus and the like or in the form of liquid preparation.

Also, there is no harm in adding other agents to the composition of this invention for preventing and treating swine dysentery.

In order to demonstrate the excellency of the composition and the method of this invention for preventing and treating swine dysentery, experimental examples are presented below in which polynactin and other active ingredients are used as singular agent.

Experimental Example 1

Experimental Procedure

A mucous bloody stool excreted by a swine infected with swine dysentery was forcibly administered to young pigs, 5 weeks old, orally at a dose of 100 g per head. One week after the artificial infection, one started to give test feed containing varied concentration of polynactin. The test feed was continuously given for one week. The polynactin used contain dinactin, trinactin and tetranactin in a proportion of 1:1:8. The concentration of polynactin in the test feed was 10 ppm, 50 ppm, 100 ppm, 500 ppm or 1000 ppm, while it was zero in the control feed. Excretion of mucous bloody stool was observed in some young pigs which were recognized as positive with regard to the infection with swine dysentery and classified into three ranks +++, ++ and + according to the extent of mucous bloody stool. Young pigs excreting no mucous bloody stool were recognized as negative with regard to dysentery.

Experimental Results

Table 2 illustrates the results of the treatment. In the group to which polynactin was not given, all the animals indicated a positive sign of swine dysentery. In the groups to which polynactin was given, the symptom of swine dysentery was mild and most of the animals were negative with regard to swine dysentery. These results demonstrate a marked therapeutic effect of polynactin on swine dysentery.

Table 2

| Concentration of polynactin (ppm) | No. of animals | Extent of Mucous bloody stool | | | | | | | |
|---|---|---|---|---|---|---|---|---|---|
| | | Before administration | | | | After administration | | | |
| | | +++ | ++ | + | − | +++ | ++ | + | − |
| 1000 | 5 | 5 | 0 | 0 | 0 | 0 | 0 | 0 | 5 |
| 500 | 5 | 4 | 1 | 0 | 0 | 0 | 0 | 0 | 5 |
| 100 | 5 | 5 | 0 | 0 | 0 | 0 | 0 | 0 | 5 |
| 50 | 5 | 5 | 0 | 0 | 0 | 0 | 0 | 1 | 4 |
| 10 | 5 | 5 | 0 | 0 | 0 | 0 | 0 | 3 | 2 |
| 0 | 5 | 4 | 1 | 0 | 0 | 5 | 0 | 0 | 0 |

Experimental Example 2

Experimental Procedure

One began to give young pigs, 5 weeks old, a feed containing the test agent three days before artificial injection, after which a mucous bloody stool of swine infected with swine dysentery was forcibly administered to the animals orally at a rate of 100 g per head. The feed containing test agent was continuously given for three weeks, after which manifestation of swine dysentery symptom was examined. Mucous bloody stool was observed in some animals, which were recognized as positive with regard to swine dysentery and classified into three ranks +++, ++ and + according to the extent of the symptom. Young pigs excreting no mucous bloody stool were recognized as negative with regard to swine dysentery. The concentration of polynactin in the test feed was 10 ppm, 50 ppm, 100 ppm, 500 ppm or 1000 ppm, while it was zero in the control feed. The polynactin used in this experiment contained dinactin, trinactin and tetranactin in a proportion of 2:3:5.

Experimental Results

Table 3 illustrates the results. In the group to which polynactin was not given, all the animals manifested the symptom of swine dysentery. In the groups to which polynactin was given, all the animals manifested no symptom of swine dysentery except for one animal to which a feed containing 10 ppm test agent was given. The results demonstrate the marked preventive effect of polynactin.

Table 3

| Concentration of polynactin (ppm) | No. of animals | Extent of mucous bloody stool | | | |
|---|---|---|---|---|---|
| | | +++ | ++ | + | − |
| 1000 | 5 | 0 | 0 | 0 | 5 |
| 500 | 5 | 0 | 0 | 0 | 5 |
| 100 | 5 | 0 | 0 | 0 | 5 |
| 50 | 5 | 0 | 0 | 0 | 5 |
| 10 | 5 | 0 | 0 | 1 | 4 |
| 0 | 5 | 4 | 1 | 0 | 0 |

Experimental Example 3

Experimental Procedure

One began to give young pigs, 5 weeks old, a feed containing test agent 3 days before artificial infection, after which one forcibly gave a mucous bloody stool of swine infected with swine dysentery orally at a rate of 100 g per head. The feed containing test agent was continuously given for three weeks, while examining the manifestation of swine dysentery.

Mucous bloody stool was observed in some of the animals which were recognized as positive with regard to swine dysentery and classified into three ranks +++, ++ and + according to the extent of symptom. Animals giving no mucous bloody stool were recognized as negative with regard to swine dysentery. The test agents used were nonactin, monactin, dinactin, trinactin, and tetranactin, all in the state of singular agent. The concentration of test agent was 10 ppm, 100 ppm or 1000 ppm.

Table 4 illustrates the results. In the group to which the test agent was not given, all the animals manifested the symptom of swine dysentery. In the group to which test agent was given, none of the animals manifested the symptom of swine dysentery, except that a mild symptom of swine dysentery was observed in the group to which 10 ppm of test agent was administered. Thus, the results demonstrate that nonactin, monactin, dinactin, trinactin and tetranactin exhibit a marked preventive effect even in the state of singular agent.

Table 4

| Name of agent | Concentration of agent (ppm) | No. of animals | Extent of mucous bloody stool | | | |
|---|---|---|---|---|---|---|
| | | | +++ | ++ | + | − |
| Nonactin | 1000 | 5 | 0 | 0 | 0 | 5 |
| | 100 | 5 | 0 | 0 | 0 | 5 |
| | 10 | 5 | 0 | 0 | 2 | 3 |
| Monactin | 1000 | 5 | 0 | 0 | 0 | 5 |
| | 100 | 5 | 0 | 0 | 0 | 5 |
| | 10 | 5 | 0 | 0 | 2 | 3 |
| Dinactin | 1000 | 5 | 0 | 0 | 0 | 5 |
| | 100 | 5 | 0 | 0 | 0 | 5 |
| | 10 | 5 | 0 | 0 | 1 | 4 |
| Trinactin | 1000 | 5 | 0 | 0 | 0 | 5 |
| | 100 | 5 | 0 | 0 | 0 | 5 |
| | 10 | 5 | 0 | 0 | 1 | 4 |
| Tetranactin | 1000 | 5 | 0 | 0 | 0 | 5 |
| | 100 | 5 | 0 | 0 | 0 | 5 |

Table 4-continued

| Name of agent | Concentration of agent (ppm) | No. of animals | Extent of mucous bloody stool +++ | ++ | + | − |
|---|---|---|---|---|---|---|
| | 10 | 5 | 0 | 0 | 1 | 4 |
| Control | 0 | 5 | 5 | 0 | 0 | 0 |

What is claimed is:

1. A method for treating swine dysentery characterized by administering, to swine, an effective quantity of one or more kinds of macrotetrolide antibiotic substances represented by the following general formula:

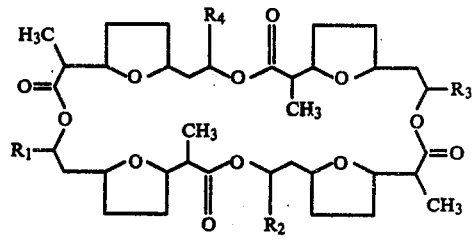

wherein $R_1$, $R_2$, $R_3$ and $R_4$ are lower alkyl groups.

2. A method for treating swine dysentery according to claim 1, wherein said lower alkyl group is methyl group or ethyl group.

3. A method for treating swine dysentery according to claim 1, wherein said macrotetrolide antibiotic substance is selected from the group consisting of nonactin, monactin, dinactin, trinactin and teranactin.

4. A method for treating swine dysentery according to claim 1, wherein said macrotetrolide antibiotic substance is polynactin.

5. A method for treating swine dysentery according to claim 1, wherein said effective quantity is 0.2 to 20 mg/day per 1 kg of the body weight of swine.

6. A method for treating swine dysentery according to claim 1, wherein said macrotetrolide antibiotic substance is orally administered to swine in the form of a mixture with feed.

7. A method for treating swine dysentery according to claim 1, wherein said macrotetrolide antibiotic substance is orally administered to swine in the form of a mixture with feed containing 10 to 1000 ppm of said macrotetrolide antibiotic substance.

* * * * *